(12) United States Patent
Montagu

(10) Patent No.: US 6,262,838 B1
(45) Date of Patent: Jul. 17, 2001

(54) FOCUSING IN MICROSCOPE SYSTEMS

(75) Inventor: Jean I. Montagu, Brookline, MA (US)

(73) Assignee: Genetic Microsystems Inc, Woburn, MA (US)

( * ) Notice: Subject to any disclaimer, the term of this patent is extended or adjusted under 35 U.S.C. 154(b) by 0 days.

(21) Appl. No.: 09/079,790

(22) Filed: May 15, 1998

Related U.S. Application Data

(63) Continuation-in-part of application No. 09/079,321, filed on May 14, 1998, and a continuation-in-part of application No. 09/045,547, filed on Mar. 20, 1998, now Pat. No. 6,201,639.
(60) Provisional application No. 60/183,021, filed on May 14, 1998.

(51) Int. Cl.[7] .................................................. G02B 21/26
(52) U.S. Cl. .......................................... 359/392; 359/391
(58) Field of Search .................................. 359/391, 392, 359/393, 394

(56) References Cited

U.S. PATENT DOCUMENTS

| | | | |
|---|---|---|---|
| 4,627,009 | 12/1986 | Holmes et al. | 364/559 |
| 4,688,908 | * 8/1987 | Moore | 359/393 |
| 4,832,474 | * 5/1989 | Yohinaga et al. | 359/393 |
| 4,891,526 | 1/1990 | Reeds | 250/442.1 |
| 5,337,178 | 8/1994 | Kung et al. | 359/393 |
| 5,351,925 | 10/1994 | Druais | 248/325 |
| 5,461,237 | * 10/1995 | Wakamoto et al. | 250/548 |
| 5,583,691 | 12/1996 | Yamane et al. | 359/393 |

* cited by examiner

Primary Examiner—Cassandra Spyrou
Assistant Examiner—Jared Treas
(74) Attorney, Agent, or Firm—Philip L. McGarrigle; Alan B. Sherr; Ivan D. Zitkovsky

(57) ABSTRACT

Microscopes, including viewing and other microscopic systems, employ a hinged, tiltable plane to adjust focus on an object such as a microscope slide. A scanning microscope under computer control, employing such a focusing action, enables unattended scanning of biochips with a simple and economical instrument. Also shown are flexure-mounting of a support plate to define the hinge axis, techniques for automatically determining position and focus, and a rotatably oscillating flying micro-objective scanner combined with the tilting plane focus system. Construction and control techniques are shown that realize simple and accurate focusing. Methods of examination of biological materials are disclosed. Simple and efficient focused scanning with a flying micro-objective of ordered arrays of nucleotides and nucleic acid fragments carried upon a microscope slide or other substrate is discovered.

42 Claims, 10 Drawing Sheets

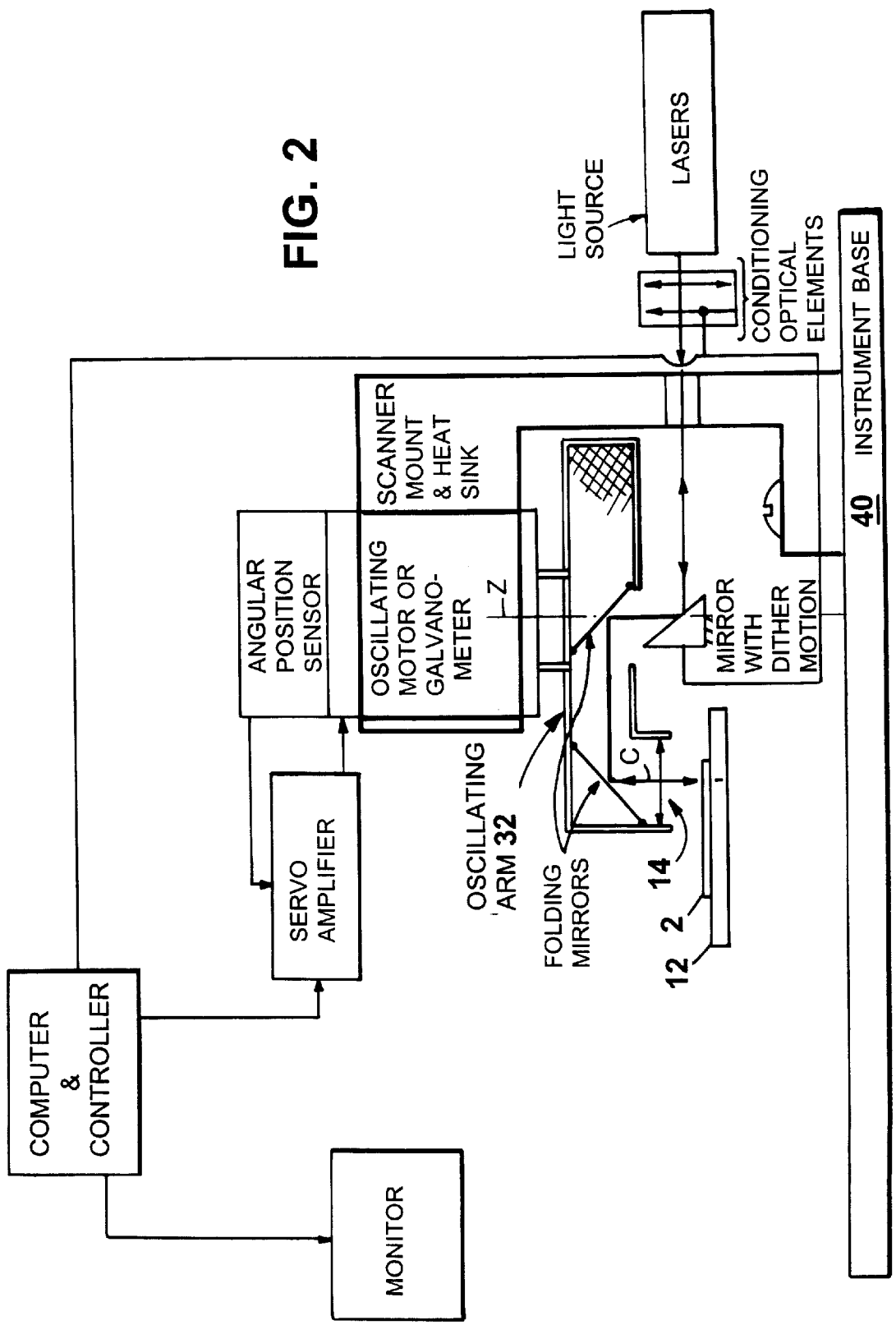

FOCUSING IN MICROSCOPE SYSTEMS

This application claims benefit to of U.S. application Ser. No. 60/183,021 filed May 14, 1998 U.S. application Ser. No. 09/079,321 CIP, filed May 14, 1998, and CIP of 09/045,547, filed Mar. 20, 1998, U.S. Pat. No. 6,201,639.

BACKGROUND OF THE INVENTION

Focusing mechanisms for microscopes are employed to position the object at the plane of focus of the instrument, to enable the object to be examined, i.e. inspected, illuminated or otherwise acted upon. Typically the object is placed upon a platform that moves laterally relative to the optical axis of the objective, to bring the area of interest of the object into alignment with the optical axis. The platform is then raised or lowered (translated) along the optical axis to achieve best focus. If it is necessary to register the optical axis with regions of the object larger than the field of view of the objective lens, the platform and object are further moved laterally in a sequence of steps to view the entire area. In some cases, microscopes are constructed to translate the objective lens or the entire microscope along the optical axis to reach best focus and in some cases the objective lens is moved laterally to bring the optical axis and areas of interest into alignment.

A known technique for translating the platform and object in the direction of the optical axis employs a precision dovetail mechanism that is activated by a manual rack and pinion or a motorized lead screw. In many cases this mechanism must be constructed with high accuracy to be capable of micron or sub-micron positional resolution, which results in high cost.

In the case of wide field of view microscopes in which lateral motion of the object or microscope objective is required, there is need for reliable, low cost and fast auto-focus mechanisms of high accuracy. This need exists particularly in respect of investigational tools for biology, e.g., for viewing arrays of fluorescently labeled microorganisms and DNA assays as well as for viewing entire biopsy samples, which may be as large as a square centimeter or larger. ("DNA" is used here to designate the full range of nucleic acids of interest to the field of biotechnology.)

According to present biological analytical technology, arrays of fluorescently labeled microorganisms and DNA assays are created in two dimensional fields. The objects to be examined in an array are, for example, DNA fragments that have discriminating sequence information. Biological laboratories have targeted objects for the arrays (e.g., spots of DNA) of diameters of the order of 25 to 250 micron, the spot size depending primarily upon the total number of objects to be represented in the array.

DNA arrays are typically probed with fluorescently labeled fragments of potentially complementary strands. When a match occurs between a fragment in a deposited spot and a fluorescently labeled fragment probe, hybridization occurs, and a positive "score" can be recorded under fluoroscopic examination. Because fluorescence, whether natural or stimulated by illumination, is a weak signal, a "score" is identified for DNA spot by the intensity of the fluorescence from the spot compared to reading(s) for the background that directly surrounds the specific spot. By controlled deposition of spots of a variety of DNA fragments in the array and by observing the matches or "scores" that occur at known spot addresses, important information concerning nucleic acids can be inferred. For this technology to expand widely, economical instruments are required that can rapidly and accurately scan the fluorescently labeled objects over a wide field of view, e.g. a field of view that is approximately 22 mm wide, the width of conventional glass microscope slides.

The large volume of data to be evaluated also calls for unattended operation of such instruments upon a sequence of slides, including automatic focusing of the microscope for each slide.

Microscopes or microscope-like instruments have been developed to inspect, illuminate or otherwise treat wide areas, based on scanning principles. In the case of inspection, the image is constructed electronically from a succession of acquired single picture elements during relative scanning movement between the object and the microscope. Focusing in these instruments is commonly automated, but there are significant economic and operational drawbacks in the systems that have been commercially available.

For a number of reasons, proper focusing is a critical need for automated microscopes where the material to be investigated is disposed over a wide area of a microscope slide. A microscope slide is typically a slab of float glass approximately 25×75 mm in x, y dimensions and about 1+0.1/−0.2 mm thick as defined by industrial standard ISO 8037-1-1986E. It is common for microscope slides to be slightly bowed, as they are not very rigid and can be deformed when clamped. In the normal installation of a slide in a microscope, the slide is caused to rest upon a flat surface and is held in place by gently pushing its edges against stops, a technique which alleviates most deformation. Other types of substrates for microscopic examination, including arrays provided on relatively thin glass cover slips and on plastic substrates, likewise have variation in thickness and are subject to deformation.

The depth of field (focus tolerance) and the resolution of a given microscope are inter-related, being defined by the laws of physics. The better the resolution, the smaller is the depth of focus. Present day biochip examination calls for pixel resolution between 5 and 10 micron which corresponds to a depth of field between approximately 30 and 200 micron, the particular values depending upon the optical configuration and the application. Since the thickness variation of commercial microscope slides is greater than this value, when the slide rests upon its back surface, auto focussing is compulsory.

In cases where the slide or other object is sufficiently uniform for the purpose at hand, auto focus is performed once per slide or object to be microscopically examined, during a setup procedure.

In some cases, automated microscopes employ dynamic focusing features, i.e. features enabling continual adjustment of focus as scanning of a given slide or object proceeds. For this purpose an algorithm is employed to define focus. Commonly, dynamic systems analyze the image acquired through the optical path of the instrument. In response to these readings, the algorithm is employed under computer control, to cause an element of the system to be raised and lowered as scanning proceeds, to translate the object along the optical axis to achieve focus in a dynamic manner. Frequently the pattern of raising and lowering is based upon a prescan of the overall object, from which positional information has been stored for use to control focus during the following examination scan. Typically instruments that enable dynamic focus adjustment with great precision require great cost.

A common attempt to avoid the cost and delays of prior art auto-focus techniques has been to incorporate a mechanism that forces a microscope slide against three buttresses, in an attempt to achieve precise location of the slide. Unfortunately, such techniques have unsatisfactory aspects, in causing the slide to deform, especially with bowing. This frequently results in loss of resolution.

SUMMARY OF THE INVENTION

The present invention provides a novel method and system for focusing a microscope. Though, at its broadest level of generality, it is applicable to all microscopes, it has particular advantage when associated in a system for automatic focusing, and it is presently considered most advantageous when the automatic focusing system is associated with a scanning system in which the object under inspection is translated under either a fixed or moving lens. The invention is especially applicable to instrument systems that operate under computer control such as optical scanners designed for reading biochips. While having a special application in achieving low cost automated scanning, in which focus is established once per slide, it also is advantageous in performing dynamic focus.

The invention provides a simple and low cost technique to bring the relevant surface (typically the top surface) of a microscope slide into the focal plane of a microscope by automatic motions of the instrument.

According to the invention, the focusing mechanism does not employ translation along the optical axis but rather simulates translation by tilting a plane on which the microscope slide is held about a defined hinge axis. It is recognized that tilting a plane about a hinge located at "infinity" can always approximate translation of a small segment of a flat plane; it is now realized that, within the range of practical microscope instrument geometry and capability, rotating a plane about a defined hinge can achieve the desired resolution for a microscope in a practical and low cost manner.

According to a preferred technique of the invention, a plane is fully determined by a line (the defined hinge) and a point. With the hinge defined to lie in a plane normal to the optical axis of the microscope, focusing is achieved by moving "the point" along a line approximately parallel to the optical axis of the microscope.

Considerations of the depth of field and the field of view of the objective of a microscope (or the properties of a scanning microscope) guide the selection of the parameters that define such a plane and its hinge and movable point.

When a reference flat microscope slide of uniform thickness is located on such a plane, the hinge and the point can be set such that a region of the top surface of the slide in registry with the optical axis of the microscope is in focus. If a flat microscope slide of different thickness is later used, adjusting only the movable point can bring the corresponding region of the top surface of that different slide into the focal plane of the objective within practical tolerances. The slide may then be advanced along the plane to bring different regions of the slide into registry with the optical axis.

Relative location of the hinge and point with respect to the optical axis of the objective is advantageously arranged to simulate the action of a lever, in which the movable point is made to move a relatively large amount compared to the resulting motion of the small segment of the plane that lies at the optical axis. As a result, a comparatively coarse, and therefore low cost, actuator, located at the long end of the lever, can be used to bring the surface of interest into focus.

A signal from a sensor can be used to servo the actuator so that the desired region of the top surface of the slide will be in the focal plane of the objective, in line with the optical axis. A number of methods, e.g. optical, capacitive or inductive, can be used to derive a signal to determine the position of the top of the slide.

Also a number of conventional techniques can be used to decide that focus has been reached. The most common techniques analyze the image quality obtained though the microscope objective to drive the actuator until the optimum position of "best focus" is reached.

In another arrangement, a mechanism is driven to press the top of a suitable region of the microscope slide against a buttress to define the desired location of the reference plane. By offsetting the buttress to a location slightly higher than that desired for best focus, the drive mechanism that rotates the plane about the hinge axis, e.g., a stepper motor driving a worm screw, can be set to rotate the plane about the hinge until the object is so pressed against the buttress that the motor stalls, thus positioning the slide at the known position of the buttress. Later the drive mechanism is retracted the exact magnitude of the known offset of the buttress from the focal plane, to position the object at the focal plane. The microscope slide is then translated laterally along the plane to bring the areas of interest into alignment with the optical axis.

In the various embodiments, when the microscope slide is mounted on a transport mechanism, the mounting surface of that mechanism is arranged to be parallel to the plane of lateral transport of the microscope slide.

In view of the above, according to one main aspect of the invention a microscope for examination or treatment of an object along an optical axis is provided, including a tiltable member defining a support plane for the object, the member being mounted to rotate about a defined hinge axis to position the object on the member at the focal plane of the microscope, the hinge axis lying in a plane substantially normal to the optical axis at a distance spaced therefrom, and a drive mechanism for rotating the member about the hinge axis is effective to bring into focus the object supported by the member.

Preferred embodiments of this aspect of the invention have one or more of the following features.

The drive mechanism is a driver located outwardly along the tiltable member, more distant from the hinge than the position in which the optical axis of the microscope intersects the tiltable member, preferably the distance of the driver from the hinge axis being greater than about twice the distance of the optical axis from the hinge axis.

The position of the drive mechanism is controlled by an automated control system. In certain preferred embodiments of this feature a buttress is disposed to be engaged by a reference portion of the object to stop the object at a position beyond the focal plane of the microscope, and a control system is arranged to retract the member back from the buttress a preset distance to align the object with the focal plane of the microscope. In other preferred embodiments of this aspect the control system includes a detector that senses the relationship of the object relative to the microscope. In certain preferred cases the detector is an optical, capacitive or inductive position sensor that senses the height of the object. In a presently particularly preferred case the detector comprises a light source and a sensor is arranged to determine the height of the object relative to the microscope on the basis of light reflected at an angle from the object. In other preferred cases a through-the-lens image analyzer is constructed and arranged to enable determination of best focus position.

The hinge is defined by a pair of spaced apart flexures that support the tiltable member, preferably the flexures being planar spring members.

A laterally movable carrier is mounted on the tiltable member, the carrier arranged to advance the object, relative to the optical axis. Preferably the direction of advances includes motion in the direction of the radius of the tiltable member. Preferably, a linear guide rail is mounted on the tiltable member, the moveable carrier member movable along the guide, the carrier member having a planar surface for supporting a planar object, the planar surface of the carrier member being parallel to the linear guide. Also, preferably, a driver is arranged to position the carrier member under computer control.

In the form of a scanning microscope, the microscope is constructed and arranged to scan in a direction transverse to the radial direction of the tiltable member, preferably the scanning microscope comprising a moving objective microscope, presently preferred being a microscope in which the moving objective is supported upon an oscillating rotary arm that describes an arc generally centered on a radial axis of the tiltable member. Preferably the objective has resolution of between about 5 and 10 micron and a depth of field of between about 30 and 200 micron.

In the form of a scanning microscope, a controller is provided, constructed to perform dynamic focus by varying the position of the drive mechanism during scanning, preferably the controller responding to through-the-objective image data, and most preferably including a system constructed to determine best focus data for an array of points during a prescan, to store this data, and to employ this data during microscopic examination of the object.

Another aspect of the invention is a microscope for examination of an object along an optical axis, which includes a tiltable member defining a support plane for the object, the member being mounted to rotate about a defined hinge axis to position the object on the member at the focal plane of the microscope, the hinge axis lying in a plane substantially normal to the optical axis at a distance spaced therefrom, and a drive mechanism for rotating the member about the hinge axis is effective to bring into focus the object supported by the member, the microscope constructed and arranged to scan in a direction transverse to the radial direction of the tiltable member, and a laterally movable carrier is mounted on the tiltable member, the carrier arranged to advance the object, relative to the optical axis, in motion in the direction of the radius of the tiltable member.

In preferred embodiments of this aspect of the invention the scanning microscope comprises a moving objective microscope, preferably in which the microscope includes a flying micro-objective lens, and preferably in which the moving objective is supported upon an oscillating rotary arm that describes an arc generally centered on a radial axis of the tiltable member.

Preferred embodiments of all of the above aspects and features of the invention are microscopes in which the depth of field is between about 30 and 200 micron, and the drive mechanism is a driver located outwardly along the tiltable member, more distant from the hinge than the position in which the optical axis of the microscope intersects the tiltable member, preferably the distance of the driver from the hinge axis being greater than about twice the distance of the optical axis from the hinge axis.

According to another aspect of the invention a method of microscopic examination is provided comprising providing a microscope for examination of an object along an optical axis, the microscope including a tiltable member defining a support plane for the object, the member being mounted to rotate about a defined hinge axis to position the object on the member at the focal plane of the microscope, the hinge axis lying in a plane substantially normal to the optical axis at a distance spaced therefrom, and a drive mechanism for rotating the member about the hinge axis, effective to bring into focus the object supported by the member, and under control of an automated control system, moving the movable member to bring the object into the plane of focus of the microscope.

Preferred embodiments of this aspect of the invention have one or more of the following features.

The object comprises biological material.

In certain cases, preferably the object fluoresces and the microscope is constructed to detect such fluorescence, and most preferably the object comprises an ordered array of nucleotides that may fluoresce, preferably the object comprises an ordered array of oligonucleotides or the object comprises an ordered array of deposits of nucleic acid fragments.

BRIEF DESCRIPTION OF THE DRAWINGS

FIG. 1 is a diagrammatic, perspective view of a scanning microscope system incorporating a tilt plane focusing mechanism, while

FIG. 2 is a diagrammatic side view of a scanning microscope system with which the focusing system of FIGS. 1–1C is combined.

FIG. 4 illustrates optical height measuring techniques that act upon the top surface of a microscope slide for detecting its position, located as shown in FIGS. 1 and 1B, while

FIG. 6 is a diagrammatic illustration of a prescan for0 dynamic focus while

DESCRIPTION OF PREFERRED EMBODIMENTS

The tilt focussing mechanism will be described as it applies to the presently preferred embodiment, in which is part of a combination that also includes an oscillating flying micro-objective scanning microscope such as shown in FIG. 2 and described in more detail in U.S. patent application 09/045,547, filed Mar. 20, 1998, which is hereby incorporated by reference.

Referring to FIG. 2, it is sufficient to note that objective-carrying arm 32 rotates in rotary oscillating fashion through an arc of e.g. 60° about rotational axis Z that is normal to the nominal plane of the microscope slide 2. The arm carries a low mass micro-objective lens 14. The optical axis C at a radial distance from the axis of rotation Z, produces a range of excursion E sufficient to scan the width of the microscope slide 2. The lens typically has a large numerical aperture. An appropriate fixed laser light source and detector are arranged to communicate with the objective lens along an optical path along the axis of rotation Z of the arm, via folding mirrors carried on the arm. In this manner the optical axis C of the lens is maintained normal to the nominal surface of the object throughout its scanning motion. While the lens is carried back and forth in its arc, the microscope slide is gradually advanced under the arc of the lens in the direction of axis Y, so that the entire slide is examined in a short time. Dither motion of a mirror in the optical path broadens the curve of the effective arc path of the lens to reduce overlap in successive scans. By suitable computer techniques, the data for the points of resolution are recorded throughout the scan of the slide and are employed to form an image by conventional computer techniques.

Figure 1:
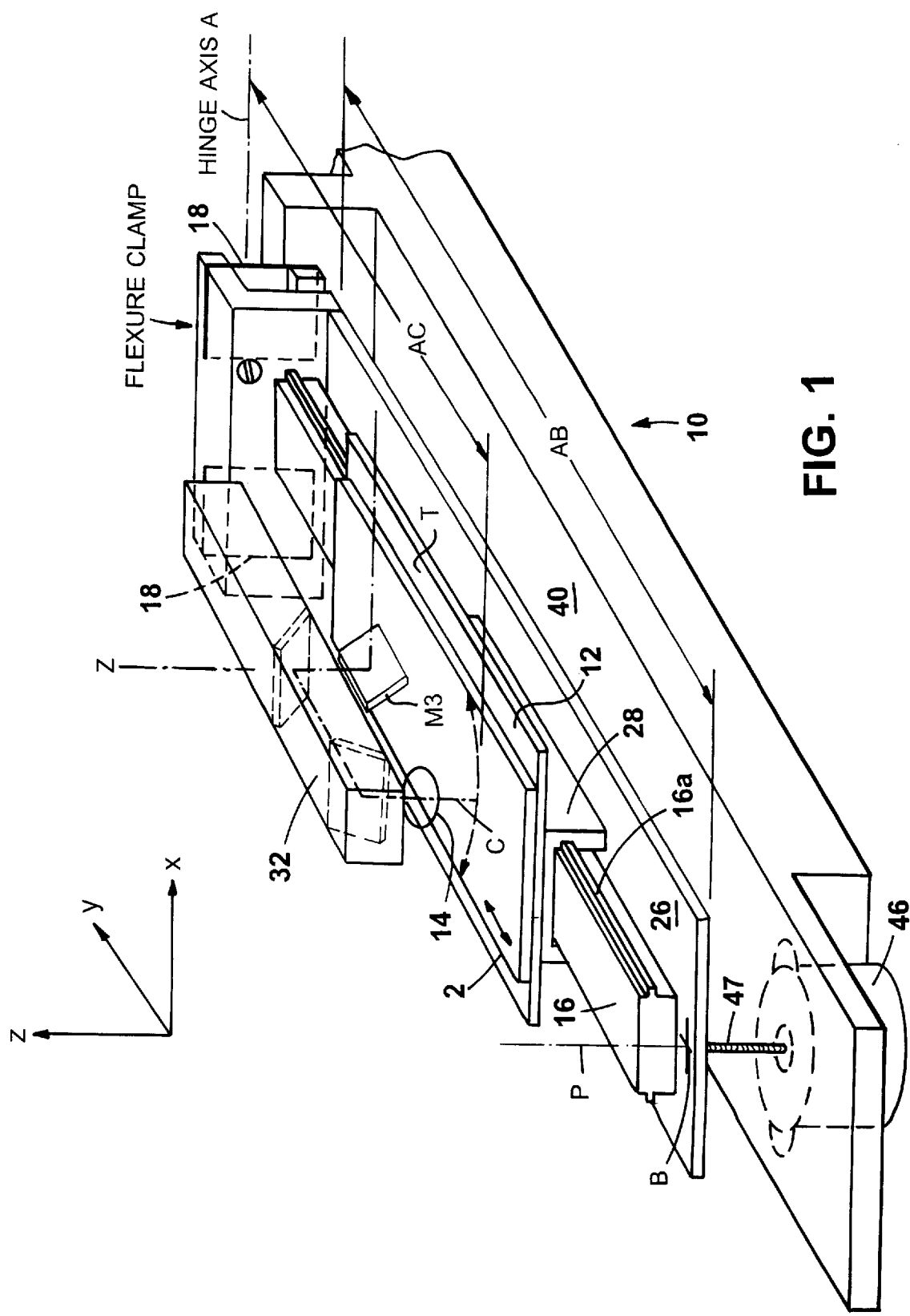
Figure 1A:
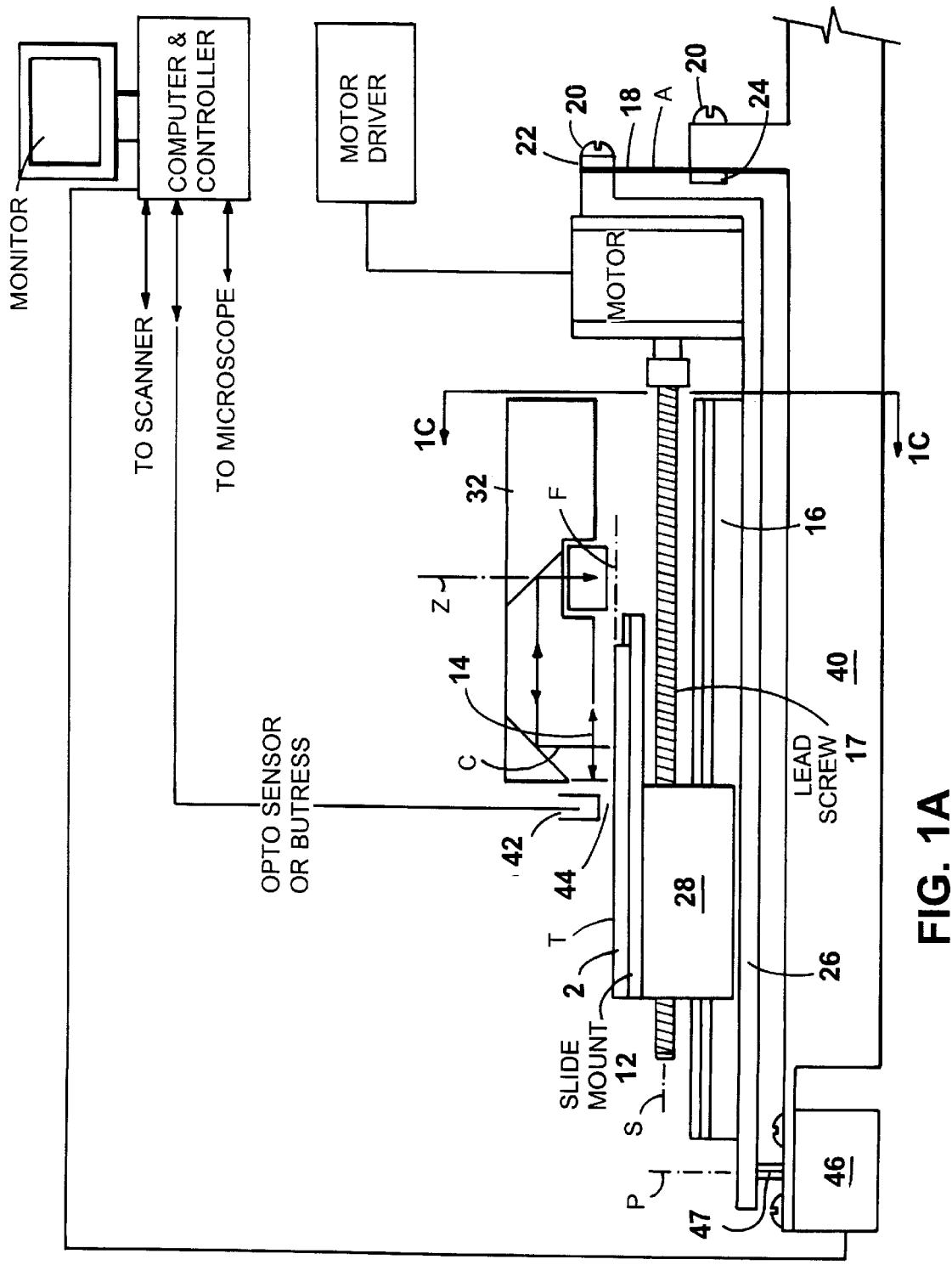
FIG. 1A is a side view.
Figure 1B:
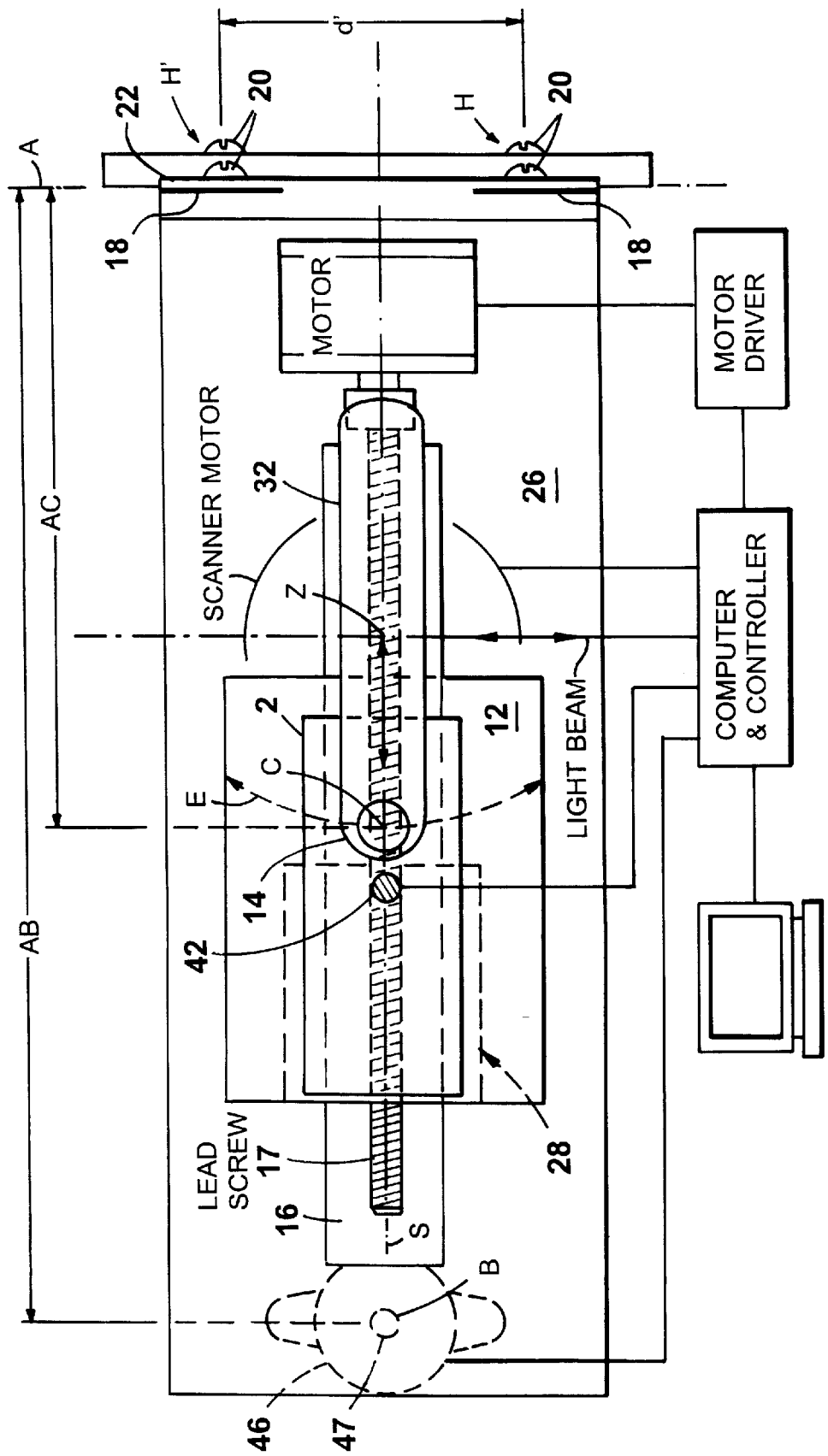
FIG. 1B is a plan view.
Figure 1C:
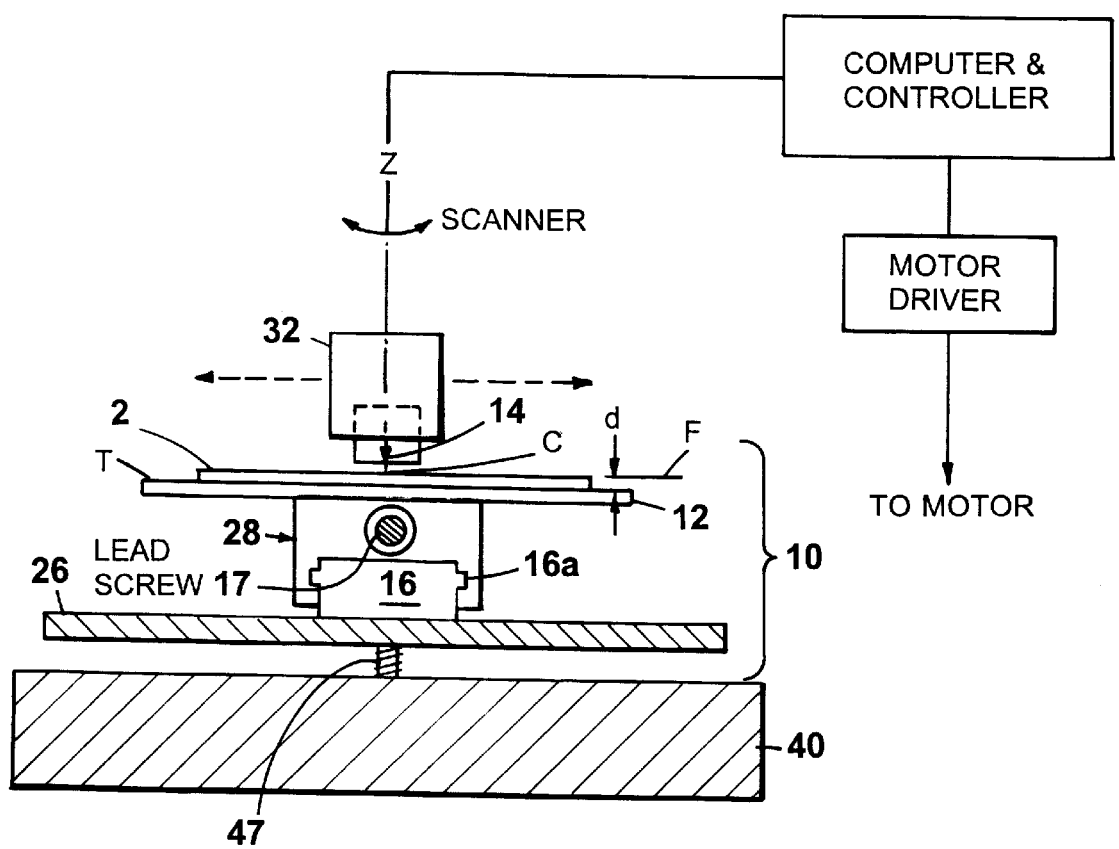
FIG. 1C is a cross sectional view of the mechanism of FIG. 1.

In the preferred embodiment of the tilt focusing mechanism 10 of FIGS. 1–1C, the microscope slide 2 is held via conventional gentle acting microscope slide holders, not shown, on slide mount platform 12. Platform 12 is itself part of moveable carriage 28, which is mounted to move axially on guide rail 16, as positioned by motor-driven lead screw 17.

Slide mount platform 12 is typically a glass plate or an anodized aluminum plate, which is installed under the objective 14 of the oscillating flying objective microscope arm 32, at a distanced (FIG. 1C) of approximately 1 mm (the nominal thickness of a microscopic slide) away from the focal plane F of the objective.

As shown in FIGS. 1 to 1C, rail 16 is mounted on hinged carrier plate 26 which is positioned in space on a 3-point mount. Two points, H and H', define hinge axis A. The optical axis C of the microscope is closer to axis A (distance AC), than is the third point B, which lies at distance AB from hinge axis A. The three points are located in a bi-symmetric fashion with respect to the axis of rotation C of the flying objective arm 32 as shown in the plan view, FIG. 1B.

Carriage 28, carrying the microscope slide, is motor driven, the motor and lead screw being shown in FIGS. 1A and 1B. The top surface T of the slide mount 12 is precisely parallel to axis S, the axis of lateral motion of the slide as defined by guide surfaces 16a of rail 16. Any deviation is equivalent to defocusing in this embodiment.

At the two points H and H', plate 26 is flexurally connected to base 40 of the instrument via flexure hinges 18, here in the form of planar sheets of spring metal that are aligned in the same plane, spaced apart distance d. The more remote third mount, B, is raised or lowered by push rod 47 for producing focus as will be described below.

As seen in the FIG. 1A side view, the respective flexures 18, at points H and H', are secured to carrier plate 26 by a holding device 20 and clamp 22. Similarly, the other end of each flexure 18 is affixed to the instrument base 40 by device 20 via clamp 24. In this embodiment the flexures establish the hinge axis in substantial alignment with the top surface of the microscope slide 2. Point B is acted upon by pusher stepper motor 46 acting through push rod 47.

To calibrate the system, a flat microscope "calibration slide" 2, fabricated with great precision, is of uniform and average special thickness of 0.95 mm, the average thickness of conventional slides. It is placed on slide mount 12 and the three points, H, H' and B are adjusted such that the top surface of slide 2 is set to be at the mid point of the focus range when translated under the objective 14 for all rotated positions of oscillating arm 32, see arm excursion range E, FIG. 1B.

In this preferred embodiment, buttress 42 (see FIGS. 1A, 1B) mounted on base 40 (its mounting structure is not shown), is adjusted such that gap 44, defined between buttress 42 and the top surface T of slide 2, permits unhindered oscillation of the scanning microscope arm 32. Gap 44 is typically 100 micron. To prepare for removal of a slide and the introduction of a new slide, pusher 46 is lowered to create a suitably large gap 44 in excess of 300 micron to prevent interference.

When a new slide 2 is introduced for inspection, to bring its top surface into the focal plane, a reference region of the slide is positioned under buttress 42, this reference region typically being the frosted section of the microscope slide that is reserved for data recording. The pusher 46 acting through push rod 47, raises plate 26 and associated parts so that this region of the top surface of the slide comes in contact with buttress 42. By suitable selection and adjustment of the pusher and its electronic driving means, pusher 46 is caused to stall when the resistance of buttress 42 is encountered, thus delivering top surface T of the slide to a precisely known reference position. Under system control, pusher 46 is then retracted a predetermined amount to bring the top surface T to the known plane of focus F, the relative position of the plane of focus to the buttress 42 having been predetermined.

The motion of point B along axis P, to achieve a given focus correction, is defined by its distance from the optical axis C of the objective as well as the location of hinge axis A with respect to the objective axis.

In the preferred case of an oscillating arm, flying objective microscope, as shown, the depth of field requirement takes into consideration the size of the field of view of the objective lens 14 (which is negligible in the preferred embodiment), the proximity of buttress 42 to optical axis C (a distance which can be made negligible), the Y axis position of the objective lens, which varies with the angular displacement of arm 32 (when the top surface of the slide is not precisely normal to optical axis C), and the position errors of the pusher mechanism 46.

Figure 3A:
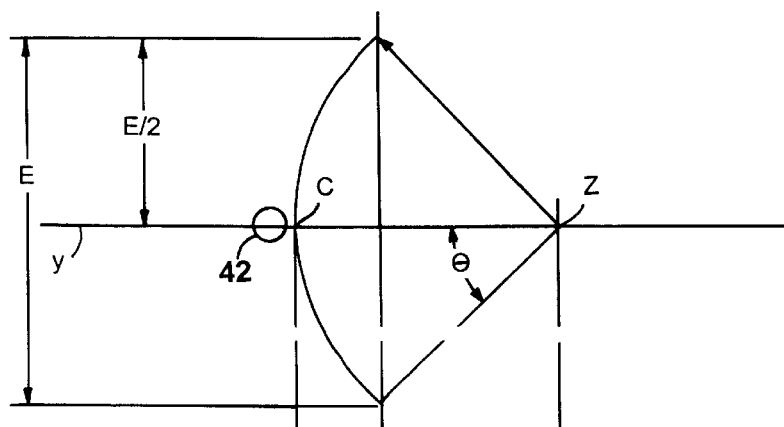
FIGS. 3A and 3B are diagrams that help define the focus variation caused by the angular oscillating motion of the scanning objective microscope of FIG. 2 associated with the tilt plane focusing mechanism of FIGS. 1–1C.
Figure 3B:
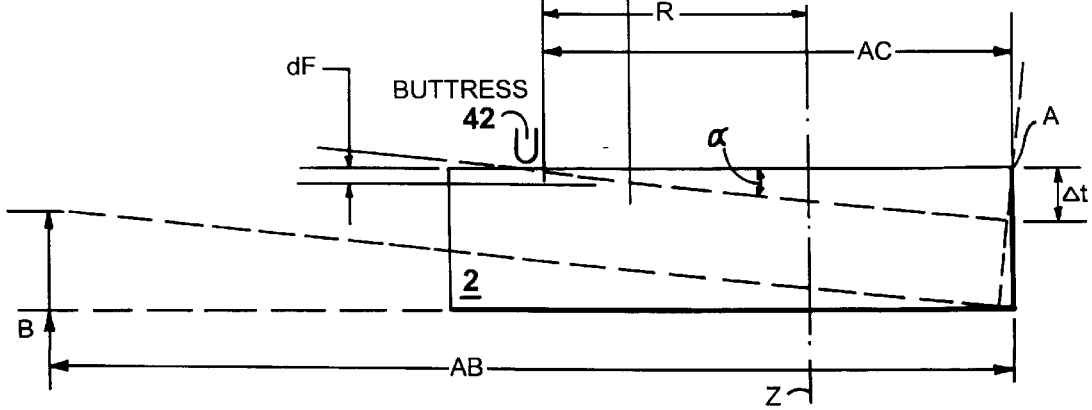

FIGS. 3A and 3B illustrate the focus variation dF as a function of angular position of arm 32 over a slide 2 tilted about axis A, in consideration of the variation in thickness permitted for standard microscope slides. It can be seen that:

$$dF = R^* \tan \alpha^* (1-\cos \theta)$$

where $\alpha$ and $\theta$ are identified on FIGS. 3A and 3B. In a specific implementation of the preferred embodiment, the following values are employed:

R=25 mm, the radial distance of objective 14 from the axis of rotation Z of the swing arm 32.

θ=+/−26 degrees, the angular excursion of arm 32 from its center position on axis Y.

AC=60 mm, the distance of the extreme position from hinge axis A of the optical axis C of the lens 14 carried on arm 32.

α=Slide thickness variation $\Delta t \div AC = +/-0.150/60 = +/-0.0025$ radian.

This produces focus variation dF=+/−6.32 micron or a total of approximately 25% of the depth of field of the objective 14 in the case at hand. (The miniature flying objective lens 14 in the case at hand has a depth of field of about 50 microns).

Figure 5A:
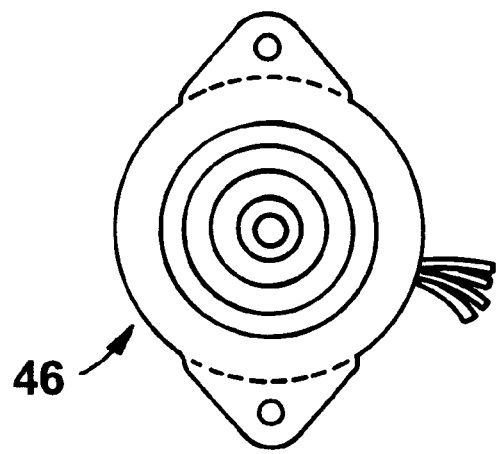
FIGS. 5A and 5B are end and side views of a linear stepper motor employed as a pusher mechanism in the system of FIGS. 1–1C and 2.
Figure 5B:
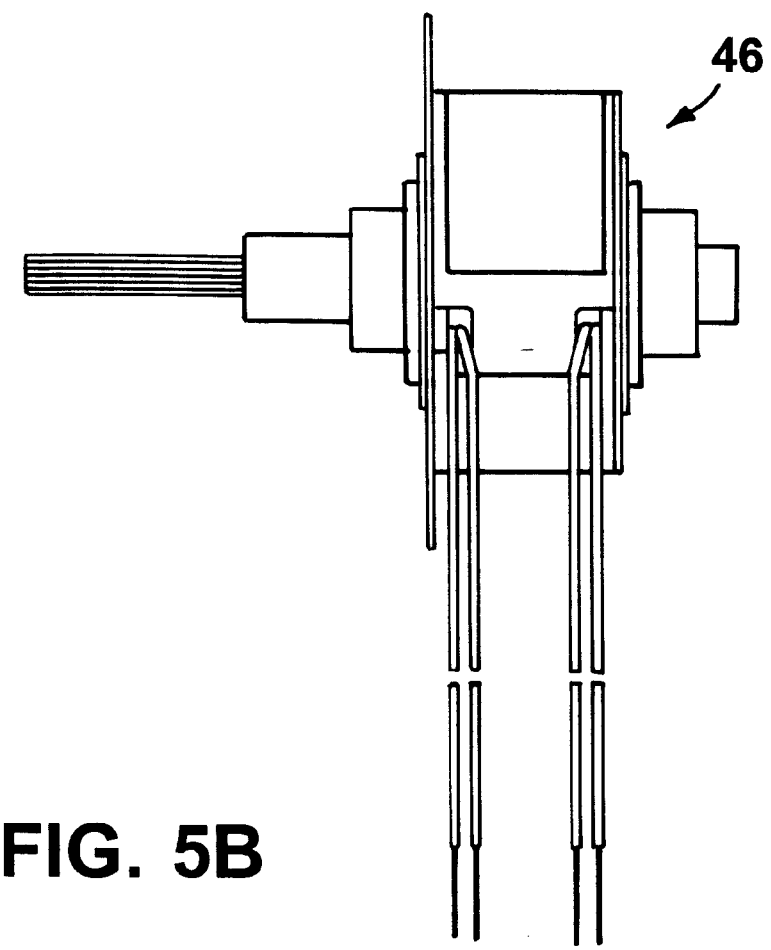

In the preferred embodiment, pusher 46 (See FIGS. 5A, 5B) is a linear stepper motor, e.g., a Haydon 3646X-V stepper motor available from Haydon Switch and Instrument, Inc. of Waterbury, Conn., having 0.0005 inch (12.5 micron) motion per step.

With the distance AB from the pusher 46 to hinge A of 150 mm, a 2.5 to 1 motion reduction is obtained, reducing the effects of any variation introduced by the pusher. The uncertainties of the digital system then cause a possible error of 5 micron of the slide position under the objective. This is approximately 10% of the budgeted focal range of the preferred embodiment. The simple and inexpensive system shown is thus capable of automatically focusing a new biochip slide when it is introduced to the system.

The system is particularly effective for examination of ordered arrays of biological material such as biochips. In one case an ordered array of oligonucleotides that may be hybridized with fluorescently labeled material is inspected. The individual specimens may be present in array densities for instance of 100 to 2000 or more specimens per square centimeter. In another case an ordered array of nucleic acid fragments is examined, for instance as deposited by the arrayer described in copending U.S. patent application, U.S. Ser. No. 09/006,344, filed Jan. 13, 1998, which is hereby incorporated by reference.

A number of modalities other than use of the buttress technique can be employed to detect the position of the top surface T of the slide or other portions of the moving mechanism. Also, the position detector and the pusher actuator may be linked as a position servomechanism.

Figure 4:
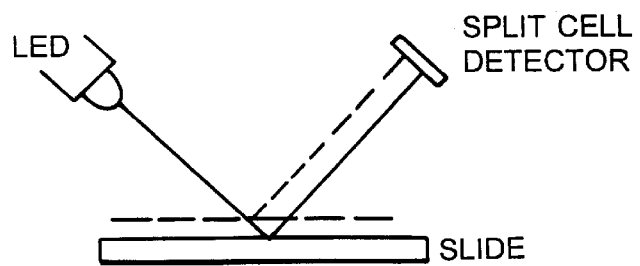

FIG. 4 exemplifies other means for detecting the height of the top surface of a slide. The system of FIG. 4 employs a light emitting diode (LED) and a split photocell detector, according to well known techniques in which light from the LED strikes the surface at an angle and is reflected to the detector, the size of the angle depending upon the proximity of the slide of the LED. The detector detects the position of the top surface essentially along the Z axis, based upon trigonometric considerations. After positioning of the slide, the control system extinguishes the LED during operation of the instrument, to avoid stray light interference. Similar embodiments employing capacitive and inductive position sensors, associated with a capacitive or inductive reference device associated with the slide, can be employed.

Figure 4A:
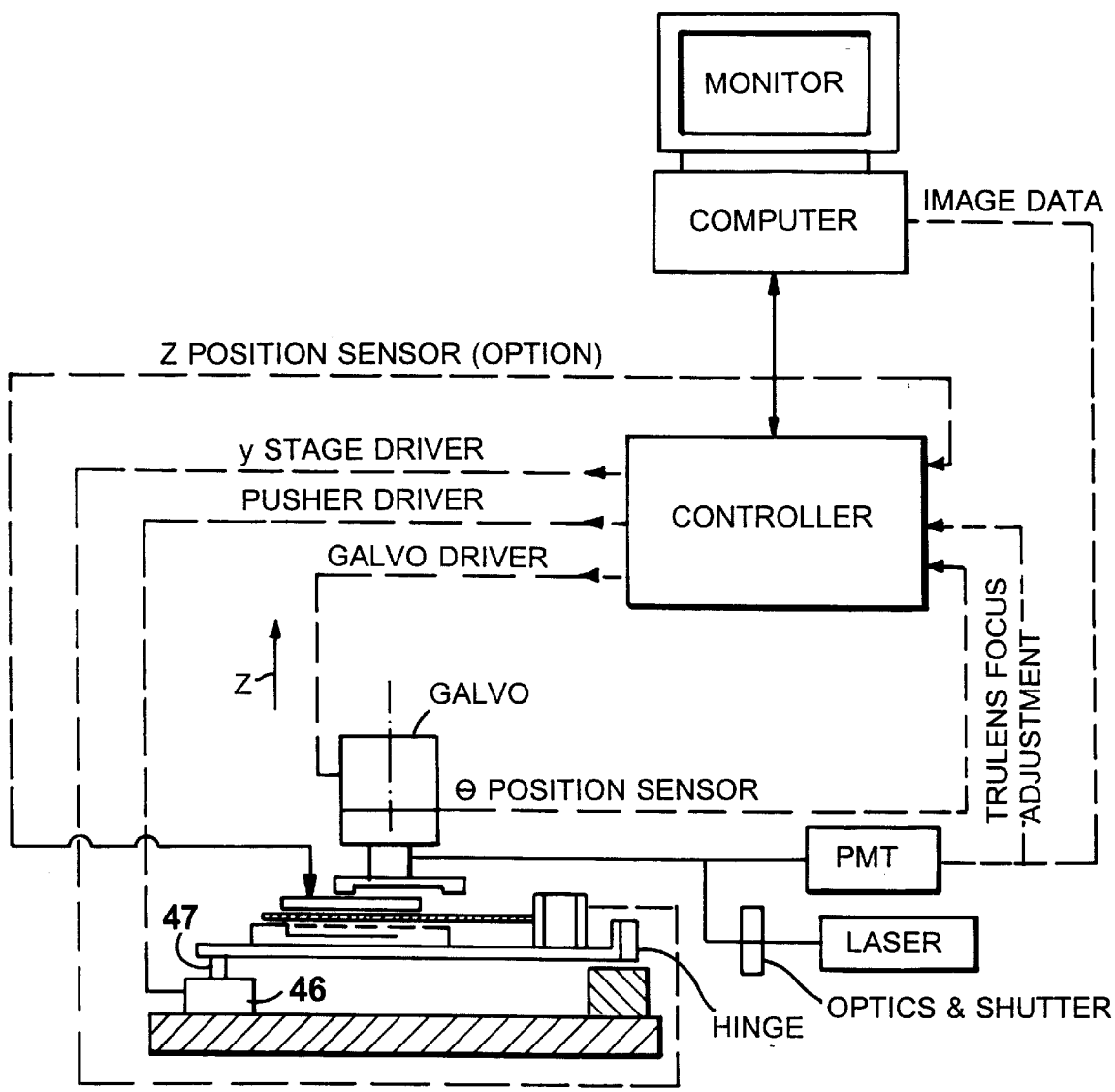
FIG. 4A is a diagram of a control system that employs the system of FIG. 4.

Referring to FIG. 4A, a detector for the height of the top surface of the slide 2, e.g. the detector of FIG. 4, feeds the Z position information, i.e. the distance of the slide from the objective, to a controller which, by servo techniques, drives the pusher 46 to bring the slide into the proper position for focus. The controller also controls the Y stage driver and the galvanometer that drives the oscillating arm 32. The controller also manages the collection of data from the objective lens which is input to a computer which receives the detected data and produces the desired image on a monitor.

The focusing technique described can advantageously be used with conventional microscopes and other types of scanning microscopes, preobjective or post objective or translation objective microscopes, etc. It also has application to other microscopic systems, such as laser illumination and laser systems for treating objects of varying dimension.

Figure 6:
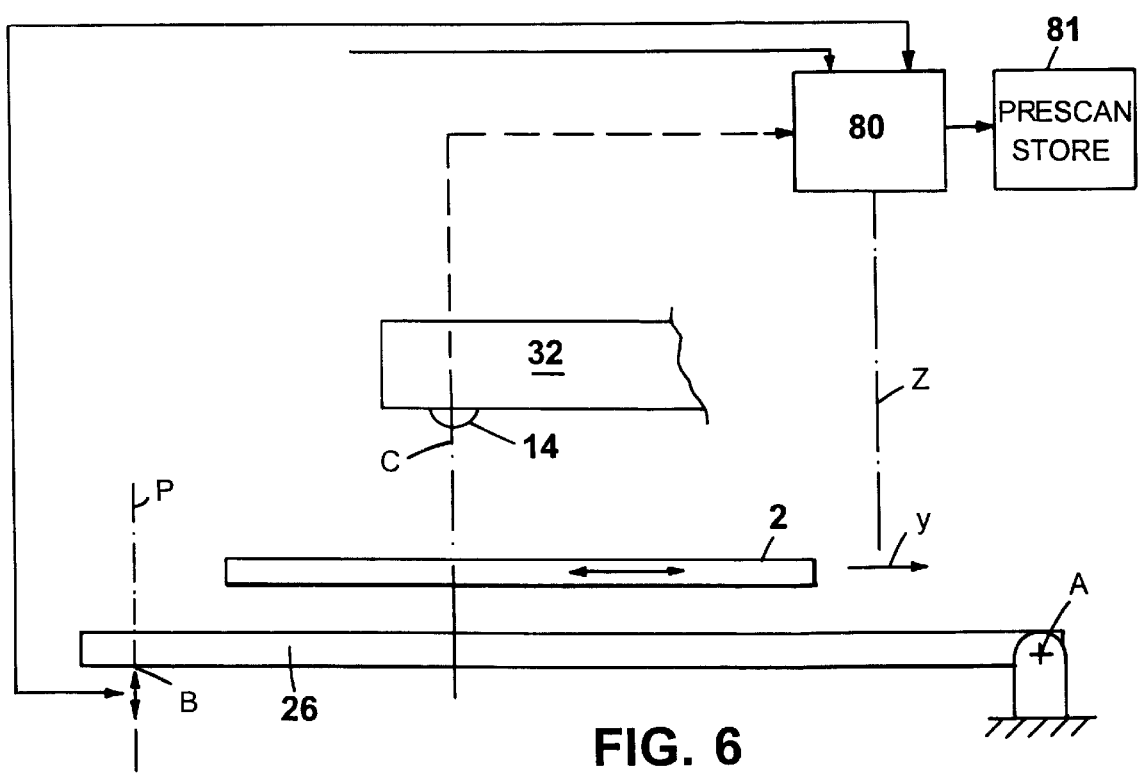

In cases where higher resolution is desired, thus limiting the depth of field of the microscope, a system similar to that of FIGS. 1 and 2 is provided that implements a dynamic focusing techniques. For example, as depicted in FIG. 6, prescan analysis of the topology of the surface of the microscope slide is performed.

The slide 2 is gradually advanced in direction Y while the flying objective lens 14 is scanned in arcs over the slide by oscillation of arm 32 about axis Z. During the prescan, the pusher 46 is exercised to dither the height of point B up and down under control of prescan analyzer 80, thus raising and lowering the object to vary focus.

By analysis of image data collected through the lens for an array of locations over the slide, the prescan analyzer determines the height of best focus for each location. This data is stored, for access during the examination scan.

Figure 6A:
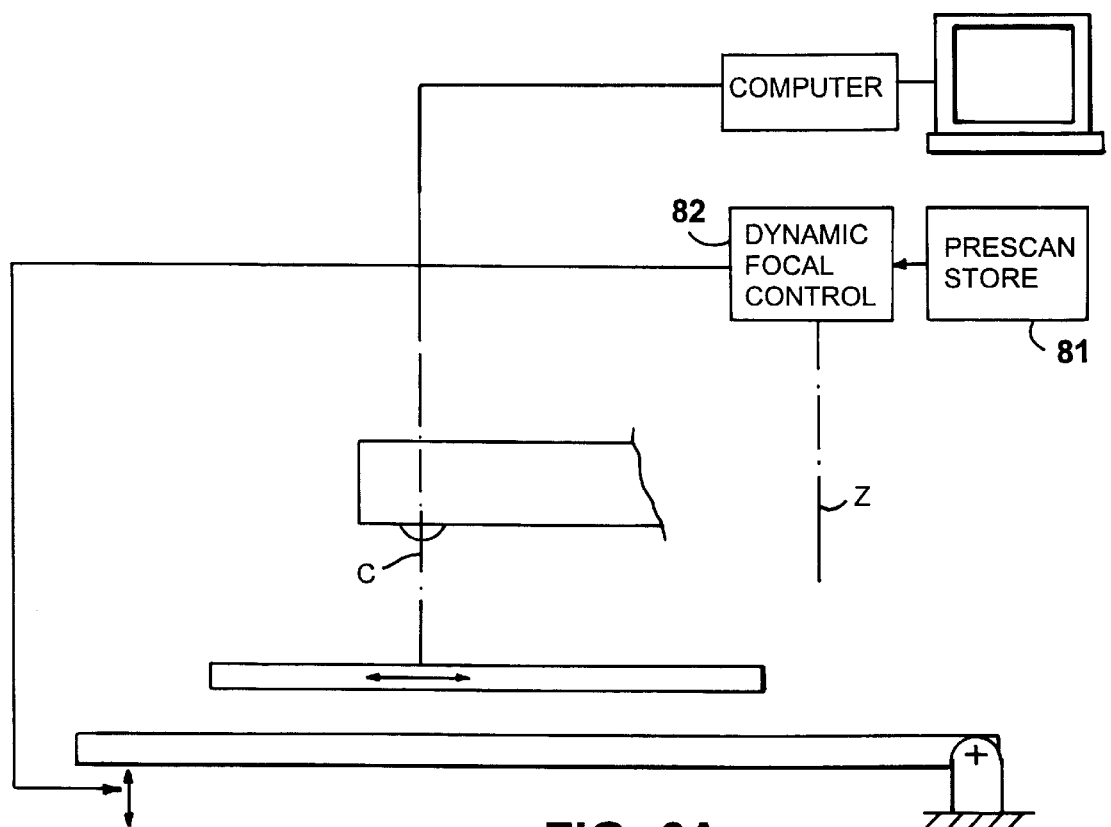
FIG. 6A is a similar diagram of the system performing dynamic focus employing stored prescan data.

One technique for doing this is by analyzing the frequency content of detected signals for features of the object imaged during prescanning, in relationship to the position of point B that is undergoing dithering. Such techniques are known, see for instance the discussion in U.S. patent application, Ser. No. 09/045,547, filed Mar. 20, 1998, which has been incorporated by reference. Thus the position of point B for best focus for a given location on the slide may be selected as that position in which high frequency content of the signal is maximized. Thus, during the prescan, a set of data is stored representing the topology of "Best Focus" over the area of the microscope slide. Referring to FIG. 6A, during the subsequent examination scan, the stored prescan data is employed by a dynamic focus controller to elevate and lower point B as the scanning proceeds to bring the respective locations on the slide into best focus.

Numerous other embodiments are of course possible and are within the scope and spirit of the claims.

What is claimed is:

1. A microscope having an objective lens with a restricted field of view about an optical axis for examination or treatment of a portion of an object lying at the optical axis, including a tiltable focusing member defining a support plane for the object, the focusing member including a flexible joint defining a pre-established hinge axis constructed to rotate in one direction to position said portion of the object at the focal plane of the microscope, the hinge axis lying in a plane substantially normal to the optical axis at a distance spaced therefrom sufficient that rotation of the portion of the object at the optical axis sufficiently approximates translation along the optical axis to enable focusing, and a drive mechanism contacting the tiltable focusing member for rotating the focusing member about the hinge axis and thereby effectively bringing into focus said portion of the object.

2. The microscope of claim 1 in which the drive mechanism is a driver located outwardly along the tiltable member, more distant from the hinge than the position in which the optical axis of the microscope intersects the tiltable member, whereby a lever effect is obtained in which a given motion of the driver results in a finer movement of the portion of the object at the optical axis.

3. The microscope of claim 2 in which the distance of the driver from the hinge axis is greater than about twice the distance of the optical axis from the hinge axis.

4. The microscope of claim 1 in which the position of the drive mechanism is controlled by an automated control system.

5. The microscope of claim 4 including a buttress disposed to be engaged by a reference portion of the object to stop the object at a position beyond the focal plane of the microscope, and a control system arranged to retract the member back from the buttress a preset distance to align the object with the focal plane of the microscope.

6. The microscope of claim 4 in which the control system includes a detector that senses the relationship of the object relative to the microscope.

7. The microscope of claim 6 in which the detector is an optical, capacitive or inductive position sensor that senses the height of the object.

8. The microscope of claim 7 in which the detector comprises a light source and a sensor arranged to determine the height of the object relative to the microscope on the basis of light reflected at an angle from the object.

9. The microscope of claim 6 in which the detector is a through-the-lens image analyzer constructed and arranged to enable determination of best focus position.

10. The microscope of claim 4 in the form of a scanning microscope having a controller constructed to perform dynamic focus by varying the position of the drive mechanism during scanning.

11. The microscope of claim 10 in which the controller responds to through-the-objective image data.

12. The microscope of claim 11 including a system constructed to determine best focus data for an array of points during a prescan, to store this data, and to employ this data during microscopic examination of the object.

13. The microscope of claim 1 in which the flexible joint is defined by two or more flexures that are planar spring members.

14. The microscope of claim 1 in which a laterally movable carrier is mounted on the tiltable focusing member, the carrier being arranged to advance the object, relative to the optical axis, in a perpendicular direction relative to the pre-established hinge axis.

15. The microscope of claim 14 in which the direction of advance includes motion in the direction of the radius of the tiltable focusing member.

16. The microscope of claim 14 in which a linear guide rail is mounted on the tiltable focusing member, the moveable carrier member being movable along the guide rail, the carrier member having a planar surface for supporting a planar object, the planar surface of the carrier member being parallel to the linear guide.

17. The microscope of claim 14 including a driver arranged to position the carrier member under computer control.

18. A scanning microscope having an objective lens with a restricted field of view about an optical axis for examination of an object lying at the optical axis, including a tiltable focusing member defining a support plane for the object, the focusing member including a flexible joint defining a pre-established hinge axis restricting rotation in one direction to position said portion of the object at the focal plane of the microscope, the hinge axis lying in a plane substantially normal to the optical axis at a distance spaced therefrom sufficient that rotation of the portion of the object sufficiently approximates translation along the optical axis to enable focusing, a drive mechanism arranged in contact with the tiltable focusing member for rotating the focusing member about the hinge axis and thereby effectively bringing into focus said portion of the object, a scanning drive mechanism to produce relative oscillating scanning motion between the object and the objective lens in a direction substantially transverse to the radial direction of the tiltable member, a photosensitive detector for detecting the stream of single picture elements provided by the objective lens, and a laterally movable carrier arranged to advance the object, relative to the optical axis, in motion substantially in the direction of the radius of the tiltable member.

19. The microscope of claim 18 in which the scanning microscope comprises a moving objective microscope.

20. The microscope of claim 19 in which the microscope includes a flying micro-objective lens.

21. The microscope of claim 19 in which the moving objective is supported upon an oscillating rotary arm that describes an arc generally centered on a radial axis of the tiltable member.

22. The microscope of claim 1 or 18 in which the depth of field of the microscope is between about 30 and 200 micron, and the drive mechanism is a driver located outwardly along the tiltable member, more distant from the hinge than the position in which the optical axis of the microscope intersects the tiltable member.

23. The microscope of claim 22 in which the distance of the driver from the hinge axis is greater than about twice the distance of the optical axis from the hinge axis.

24. The scanning microscope of claim 18, 20 or 21 in which the scanning drive mechanism is a limited rotation oscillating motor operating at a substantial frequency.

25. The scanning mechanism of claim 24 in the form of a fluorescence detection microscope.

26. A method of microscopic examination comprising providing a microscope having an objective lens with a restricted field of view about an optical axis for examination of a portion of an object lying at the optical axis, the microscope including a tiltable focusing member defining a support plane for the object, the focusing member including a flexible joint defining a pre-established hinge axis restricting rotation in one direction to position said portion of the object at the focal plane of the microscope, the hinge axis lying in a plane substantially normal to the optical axis at a distance spaced therefrom sufficient that rotation of the portion of the object sufficiently approximates translation along the optical axis to enable focusing, and a drive mechanism in contact with the tiltable focusing member for rotating the focusing member about the hinge axis and thereby effectively bringing into focus said portion of the object, and under control of an automated control system, moving the tiltable focusing member to bring the portion of the object into the plane of focus of the microscope.

27. The method of claim 26 in which the object comprises biological material.

28. The method of claim 27 in which the object fluoresces and the microscope is constructed to detect such fluorescence.

29. The method of claim 28 in which the object comprises an ordered array of nucleotides that may fluoresce.

30. The method of claim 28 in which the object comprises an ordered array of oligonucleotides.

31. The method of claim 28 in which the object comprises an ordered array of deposits of nucleic acid fragments.

32. The method of claim 26 in which the microscope is a scanning microscope and includes a drive mechanism for rotating the focusing member about the hinge axis, effective to bring into focus said portion of the object, drive mechanism to produce relative oscillating scanning motion between the object and the objective lens in a direction transverse to the radial direction of the tiltable member and a photosensitive detector for detecting the stream of picture elements produced by the objective lens.

33. The method of claim 32 in which the microscope is constructed and arranged to repeatedly scan in a direction transverse to the radial direction of the tiltable member, and a laterally movable carrier mounted on the tiltable member, the carrier arranged to advance the object, relative to the optical axis, in motion in the direction of the radius of the tiltable member.

34. A scanning microscope having an objective lens with a restricted field of view about an optical axis for examination of a portion of an object lying at the optical axis one picture element at a time, including a tiltable focusing member defining a support plane for the object, the focusing member including a flexible joint defining a pre-established hinge axis restricting rotation in one direction to position said portion of the object at the focal plane of the microscope, the hinge axis lying in a plane substantially normal to the optical axis at a distance spaced therefrom sufficient that rotation of the portion of the object sufficiently approximates translation along the optical axis to enable focusing, a drive mechanism arranged to displace linearly the tiltable focusing member for rotating the focusing member about the hinge axis and thereby effectively bringing into focus said portion of the object, a scanning drive mechanism constructed and arranged to produce relative oscillating scanning motion between the object and the objective lens in a direction substantially transverse to the radial direction of the tiltable member, and a photosensitive detector for detecting the stream of picture elements received from the objective lens as it is scanned over the object.

35. The microscope of claim 34 in which the scanning microscope comprises a moving objective microscope.

36. The microscope of claim 35 in which the moving objective is supported upon an oscillating rotary arm that describes an arc generally centered on a radial axis of the tiltable member.

37. The microscope of claim 34 in which the objective has resolution of less than about 10 micron and a depth of field of less than 200 micron.

38. A tilt focusing mechanism comprising:
   a tiltable focusing member including a support constructed to receive an object;
   a rotation structure including a flexure having a pre-established hinge axis defining rotation in one direction, said pre-established hinge axis being at a first distance spaced from an optical axis of an objective lens; and
   a drive mechanism including a displacement member constructed and arranged to rotationally displace said support in said direction about said pre-established hinge axis and thereby effectively bring into focus a portion of the object with respect to the objective lens, said displacement member being located from said optical axis at a second distance being larger than said first distance.

39. The tilt focusing mechanism of claim 38 wherein said displacement member comprises a push rod.

40. The tilt focusing mechanism of claim 38 wherein said flexure is mechanically coupled to said tiltable focusing member.

41. The tilt focusing mechanism of claim 38 wherein said tiltable focusing member further includes a laterally movable carrier constructed and arranged to advance said object relative to the optical axis of said objective lens.

42. The tilt focusing mechanism of claim 41 wherein said objective lens is mounted on a scanning drive mechanism constructed and arranged to produce relative oscillating scanning motion between the object and said objective lens, said scanning motion being in a direction substantially transverse to a radial direction defined by said hinge axis and said displacement member.

* * * * *